(12) United States Patent
Yamada et al.

(10) Patent No.: US 7,098,655 B2
(45) Date of Patent: Aug. 29, 2006

(54) EDDY-CURRENT SENSOR WITH PLANAR MEANDER EXCITING COIL AND SPIN VALVE MAGNETORESISTIVE ELEMENT FOR NONDESTRUCTIVE TESTING

(75) Inventors: Sotoshi Yamada, Ishikawa (JP); Shigeru Shoji, Tokyo (JP)

(73) Assignees: Kanazawa University, Ishikawa (JP); TDK Corporation, Tokyo (JP)

( * ) Notice: Subject to any disclaimer, the term of this patent is extended or adjusted under 35 U.S.C. 154(b) by 176 days.

(21) Appl. No.: 10/810,713

(22) Filed: Mar. 29, 2004

(65) Prior Publication Data

US 2005/0140355 A1 Jun. 30, 2005

(30) Foreign Application Priority Data

Jul. 22, 2003 (JP) ............... 2003-277355

(51) Int. Cl.
G01N 27/82 (2006.01)
G01R 33/09 (2006.01)

(52) U.S. Cl. .................. 324/235; 324/238; 324/240

(58) Field of Classification Search ................ 324/235, 324/252, 234, 236–243
See application file for complete search history.

(56) References Cited

U.S. PATENT DOCUMENTS

| | | | | |
|---|---|---|---|---|
| 5,747,988 A | * | 5/1998 | Suzuma ................ | 324/232 |
| 6,150,809 A | * | 11/2000 | Tiernan et al. ........... | 324/238 |
| 6,888,346 B1 | * | 5/2005 | Wincheski et al. ....... | 324/235 |

FOREIGN PATENT DOCUMENTS

| | | |
|---|---|---|
| JP | 7-83884 | 3/1995 |
| JP | 9-189682 | 7/1997 |
| JP | 11-248685 | 9/1999 |
| JP | 2000-80535 | 3/2000 |
| JP | 2002-90490 | 3/2002 |

OTHER PUBLICATIONS

Y. Kataoka, et al. "Application of GMR Line Sensor to Eddy Current Testing Probe", Journal of the Magnetics Society of Japan, vol. 27, No. 4, pp. 385-388, Apr. 1, 2003.
Y. Kataoka, et al. "Application of GMR Line Sensor to Eddy Current Testing", Digests of Intermag 2003, IEEE, CQ-07, Apr. 2003.
Sotoshi Yamada, et al. "Inspection of Bare Printed Circuit Board Using Planar Type ECT Probe", Review of Progress in Quantitative NDE, p. 9, Jul. 28, 2003.
Yuzo Fukuda, et al. "High Frequency and Small Field Amplitude Characteristics of GMR-SV Sensor for Eddy Current Testing", The 27th Annual Conference of Magnetics in Japan, 19pC-1, p. 472, Sep. 19, 2003.
K. Chomusuwan, et al. "The GMR Sensor Utilization for PCB Inspection Based on Eddy-Current Testing Technique", The 27th Annual Conference of Magnetics in Japan, 19pC-2, p. 473, Sep. 19, 2003.

(Continued)

Primary Examiner—Jay M. Patidar
(74) Attorney, Agent, or Firm—Oblon, Spivak, McClelland, Maier & Neustadt, P.C.

(57) ABSTRACT

An eddy-current sensor for nondestructive testing according to the present invention includes a planar exciting coil having a pair of current lines in parallel with each other through which exciting currents flow in opposite directions to each other during the testing, for generating an alternative magnetic field applied to a subject to be nondestructively tested by the exciting currents, and at least one MR element positioned on a central axis between the pair of current lines and on the opposite side to the subject in relation to the exciting coil, for detecting a magnetic field generated newly from the subject by an eddy-current induced by the alternative magnetic field.

10 Claims, 4 Drawing Sheets

OTHER PUBLICATIONS

Y. Fukuda, et al. "High-Frequency, Low-Amplitude Magnetic Field Characteristics of SV-GMR Sensor for ECT Technique", Journal of the Magnetics Society of Japan, vol. 28, No. 3, pp. 405-408, Mar. 1, 2004.

K. Chomsuwan, et al. "GMR Sensor Utilization for PCB Inspection Based on the Eddy-Current Testing Technique", Transactions of the Magnetics Society of Japan, vol. 4, No. 1, pp. 39-42, Feb. 1, 2004.

T. Miyagoshi, et al. "Feasibility of Inspecting Defects in Printed Circuit Boards by Using Eddy-Current Testing Techniques", Journal of the Magnetics Society of Japan, vol. 23, No. 4-2, pp. 1613-1616, 1999.

S. Yamada, et al. "Trend of Detection Techniques Using Planar-Type Micro-Eddy-Current Testing Probes", Journal of the Magnetics Society of Japan, vol. 23, No. 7, pp. 1817-1825, 1999.

Kazunori Nakamura, et al., "ECT Multi-Sensor for Inspection of Printed Circuit Boards", The 15th Symposium on Electromagnetic and Dynamics, May 28, 2003, pp. 339-342 (with English Abstract).

Yasuhiro Kataoka, et al., "Detection of Eddy Current Change by Slit using GMR Line Sensor", The Papers of Technical Meeting on Magnetics, IEEE Japan (MAG), MAG-02, No. 131-136, Oct. 23, 2002, pp. 11-16 (with English Abstract).

* cited by examiner

EDDY-CURRENT SENSOR WITH PLANAR MEANDER EXCITING COIL AND SPIN VALVE MAGNETORESISTIVE ELEMENT FOR NONDESTRUCTIVE TESTING

BACKGROUND OF THE INVENTION

1. Field of the Invention

The present invention relates to an eddy-current sensor for nondestructive testing used for detecting object's shapes, defects and so on nondestructively.

2. Description of the Related Art

Eddy-current testing (ECT) technique is frequently utilized for nondestructive testing of important metal machine parts used in a nuclear power plant, an aircraft, and so on. Generally, such an ECT probe for nondestructive testing using the eddy-current includes mainly an exciting coil and a detector coil for detecting a magnetic field based on an eddy-current induced by an alternating magnetic field generated by the excited coil. Such a technique is described in for example, Japanese Patent Publications Nos. 07-083884A, 09-189682A, 11-248685A and 2002-090490A.

Further, some of the inventors propose an ECT probe for inspecting printed circuit boards, including a meander-type exciting coil and a figure-of-eight-type pick-up coil for the eddy-current detection, described in for example, T. Miyagoshi, D. Kacprzak, S. Yamada and M. Iwahara, "Feasibility of Inspecting Defects in Printed Circuit Boards by Using Eddy-Current Testing Techniques", Journal of the Magnetics Society of Japan, Vol.23, No.4–2, pp. 1613–1616, 1999, and S. Yamada and M. Iwahara, "Trend of Detection Techniques Using Planar-Type Micro-Eddy-Current Testing Probes", Journal of the Magnetics Society of Japan, Vol.23, No.7, pp.1817–1825, 1999.

Because the above-mentioned conventional ECT probe uses a coil as a means of detecting the magnetic field based on the eddy-current, it has a limit of miniaturization and sensitivity improvement. That is, the detection coil has a certain amount of length, width and thickness. Therefore, the conventional ECT probe has been practically able to detect only relatively large defects and changes in the order of millimeter or more.

Recently, the ECT probe, however, has been largely required to be used for very fine testing such as an inspection of micro-defects on an object's surface and an inspection of micropatterns of a printed circuit board. The following problems occur when the ECT probe with the conventional structure is used for the purpose to meet such a requirement:

(a) The conventional ECT probe has a physical limit for reducing the number of turns in the detection coil, a diameter of the coil and a coil length in order to improve its resolution;

(b) The probe's sensitivity decreases by reducing the number of turns in the coil, a diameter of the coil and a coil length in order to improve its resolution, because coil's sensitivity is proportional to a coil's cross-section and the number of turns in the coil;

(c) The sensitivity decrease damages reliability of signals themselves because the decrease lowers the signal-to-noise ratio.

Especially, when the detection coil is set on the opposite side to a subject in relation to the exciting coil in order to prevent a protrusion from being formed on the near side to the subject in relation to the exciting coil, no high-reliability test is expected to be performed without the detection coil more sensitive.

BRIEF SUMMARY OF THE INVENTION

It is therefore an object of the present invention to provide an eddy-current sensor for nondestructive testing, possessing both very high performances of sensitivity and resolution.

Another object of the present invention is to provide an eddy-current sensor for nondestructive testing, showing high response speed.

According to the present invention, an eddy-current sensor for nondestructive testing is provided, which comprises a planar exciting coil at least having a pair of current lines in parallel with each other through which exciting currents flow in opposite directions to each other during the testing, for generating an alternative magnetic field applied to a subject to be nondestructively tested by the exciting currents, and at least one magnetoresistive (MR) element positioned on a central axis between the pair of current lines and on the opposite side to the subject in relation to the exciting coil, for detecting a magnetic field generated newly from the subject by an eddy-current induced by the alternative magnetic field.

The MR element is used as a means of detecting the magnetic field generated by the change of the eddy-current. Therefore, only a slight change of the eddy-current direction can be detected with greatly high sensitivity, even when the MR element is set on the opposite side to the subject in relation to the exciting coil in order to prevent a protrusion from being formed on the near side to the subject. Further, a detecting resolution can also be highly improved because of the great miniaturization of the detecting means. Furthermore, because the element has a small magnetic moment and an excellent magnetic response, an exciting frequency can be set at a high value. Therefore, a high speed scanning can be performed, and a testing speed under higher resolution can be prevented from decreasing. Consequently, nondestructive testing showing high sensitivity, high testing speed, high resolution and high reliability with high signal-noise ratio can be performed.

Preferably, the at least one MR element is at least one giant magnetoresistive (GMR) element such as, for example, a spin-valve magnetoresistive (SVMR) element or at least one tunnel magnetoresistive (TMR) element.

Preferably, each of the at least one GMR element or the at least one TMR element comprises a multilayered film laminated in parallel with a planar plane of the exciting coil.

More preferably, the multilayered film includes a pinned-magnetization-direction layer (pinned layer), and the pinned layer is magnetized in parallel with a pair of current lines.

It is much more preferable that the multilayered film includes a free-magnetization-direction layer (free layer), and the free layer under the condition without any external magnetic field is magnetized perpendicularly to a pair of current lines.

Preferably, the at least one MR element comprises a chip substrate, a single magnetoresistor formed on the chip substrate, and at least one thin-film chip each of which has a pair of electrode terminals connected to both ends of the single magnetoresistor, and at least one thin-film chip is bonded on the exciting coil.

It is also preferable that the at least one MR element is a single MR element or a plurality of MR elements aligned on a central axis between a pair of current lines.

Preferably, the at least one MR element comprises a chip substrate, a plurality of magnetoresistors formed on the chip substrate, and at least one thin-film chip each of which has a plurality of pairs of electrode terminals connected respectively to both ends of a plurality of magnetoresistors, and at least one thin-film chip is bonded on the exciting coil.

In this embodiment, the at least one thin-film chip is preferably a single thin-film chip or a plurality of thin-film chips, aligned on a central axis between a pair of current lines.

Preferably, the exciting coil is a meander-type coil.

It is also preferable the exciting coil comprises a coil conductor layer formed on a substrate and an insulating layer covering the coil conductor layer.

Further objects and advantages of the present invention will be apparent from the following description of the preferred embodiments of the invention as illustrated in the accompanying drawings.

DETAILED DESCRIPTION OF THE INVENTION

Figure 1:
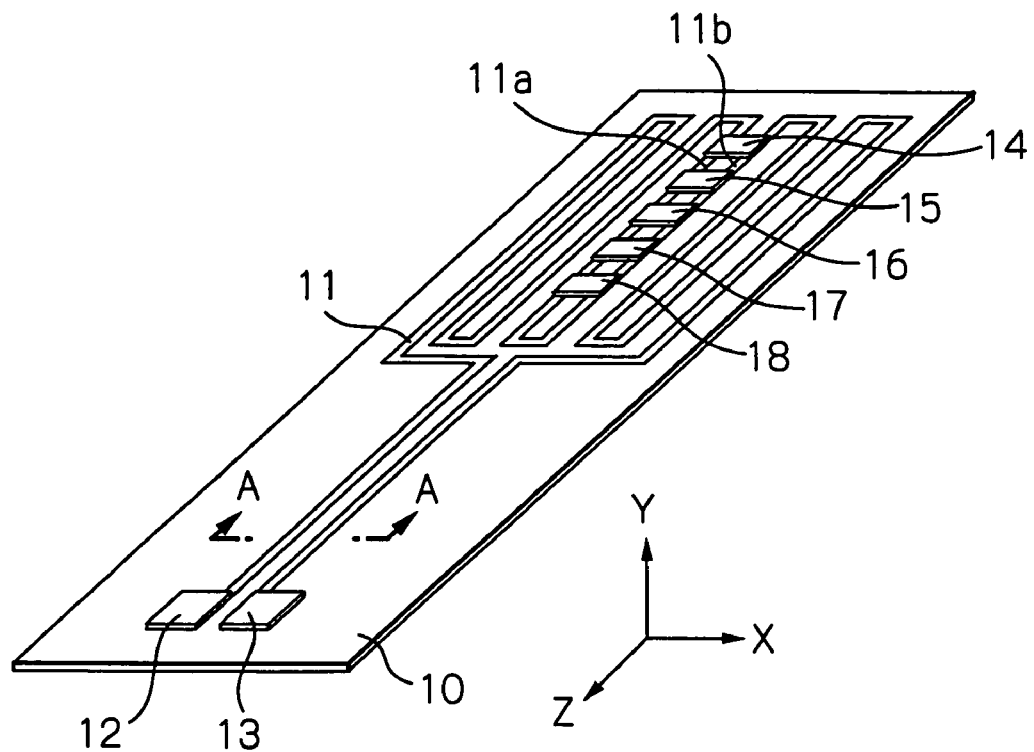
FIG. 1 shows a perspective view schematically illustrating a configuration of an eddy-current sensor for nondestructive testing according to a preferred embodiment of the present invention.
Figure 2:
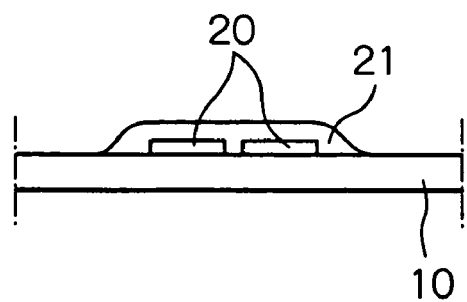
FIG. 2 shows a cross-sectional view taken along line A-A shown in FIG. 1.

FIG. 1 shows a perspective view schematically illustrating a configuration of an eddy-current sensor for nondestructive testing according to a preferred embodiment of the present invention, and FIG. 2 shows a cross-sectional view taken along line A-A shown in FIG. 1.

In these figures, reference numeral 10 indicates a substrate formed of insulating material, 11 indicates a meander-type exciting coil including coil conductors formed as the planar pattern turned back on substrate 10, 12 and 13 indicate a pair of electrode terminals connected electrically to both ends of the exciting coil 11, and 14 to 18 indicate thin-film chips bonded on the exciting coil 11 each of which is mounted with a GMR element such as an SVMR element respectively.

The exciting coil 11 includes a coil conductor layer 20 formed on the insulative substrate 10 and an insulating layer 21 covering the coil conductor layer 20, as clarified from FIG. 2. An exciting part of the exciting coil 11 has a plurality of current lines that extend in parallel with each other to Z direction on the substrate 10, and are turned back at both ends. During the testing, alternative exciting currents with opposite directions to each other flow through the current lines adjacent to each other, respectively.

The thin-film chips 14 to 18 are aligned on a central axis of a pair of current lines 11a and 11b positioned at the center in the X direction on the exciting coil 11. The surface opposite to a visible surface of the substrate 10 in FIG. 1 faces a subject. Therefore, the thin-film chips 14 to 18 are bonded on the opposite surface to the subject in relation to the exciting coil 11.

Figure 3:
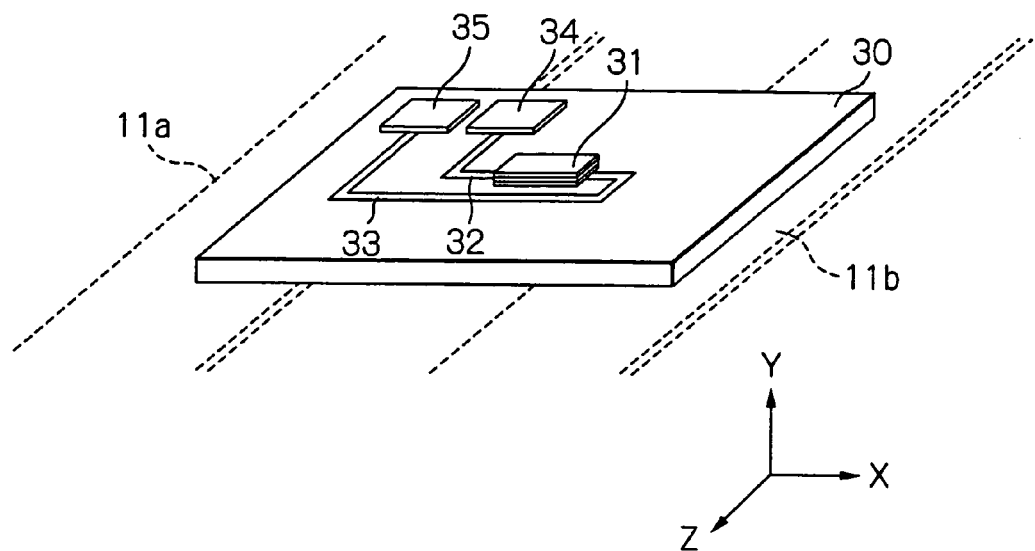
FIG. 3 shows a perspective view schematically illustrating a configuration of each thin-film chip according to the embodiment shown in FIG. 1.

FIG. 3 shows a perspective view schematically illustrating a configuration of each thin-film chip according to the present embodiment. To be easily understood, the GMR elements are described with exaggeration in FIG. 3.

Each of the thin-film chips 14 to 18 includes, for example, a GMR element 31 such as an SVMR element, a pair of lead conductors 32 and 33 connected electrically to the GMR element 31, and a pair of electrode terminals 34 and 35 connected electrically to the lead conductors 32 and 33, all of which are formed by thin-film technique on a chip substrate 30.

Figure 4A:
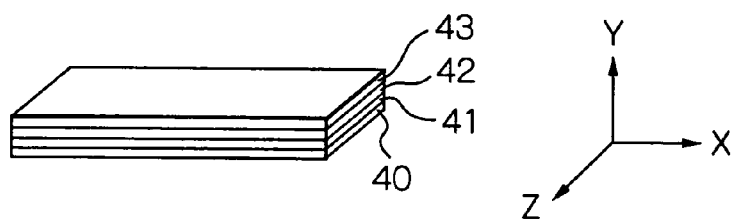
FIGS. 4a and 4b show perspective views schematically illustrating two film-structure examples of a main part of an SVMR element for an example of the GMR element shown in FIG. 3.
Figure 4B:
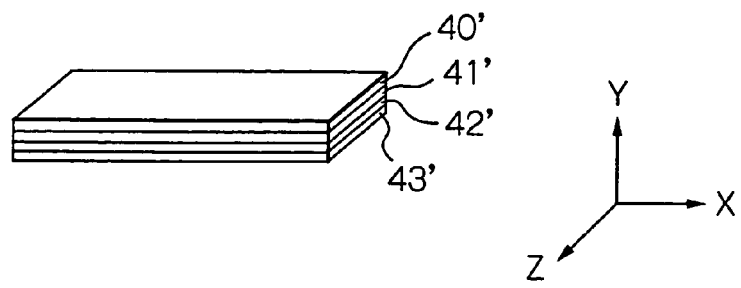

FIGS. 4a and 4b show perspective views schematically illustrating two film-structure examples of a main part of an SVMR element for an example of the GMR element 31.

In the film-structure example shown in FIG. 4a, the main part of the SVMR element is formed of an SVMR multilayered film in which a free layer 40 made of a ferromagnetic material, a spacer layer 41 made of a non-magnetic conductive material, a pinned layer 42 made of a ferromagnetic material and a pinning layer 43 made of an antiferromagnetic material are laminated in this order from the substrate side. In the SVMR multilayered film, the pinned layer 42 and the pinning layer 43 are magnetized to the in-plane −Z direction of the layers, and the free layer 40 under the condition without any external magnetic field is magnetized to the in-plane +X direction of the layer.

In the film-structure example shown in FIG. 4b, the main part of the SVMR element is formed of an SVMR multilayered film in which a pinning layer 43' made of an antiferromagnetic material, a pinned layer 42' made of a ferromagnetic material, a spacer layer 41' made of a non-magnetic conductive material and a free layer 40' made of a ferromagnetic material are laminated in this order from the substrate side. In the SVMR multilayered film, the pinned layer 42' and the pinning layer 43' are magnetized to the in-plane −Z direction of the layers, and the free layer 40' under the condition without any external magnetic field is magnetized to the in-plane +X direction of the layer.

The SVMR element formed of such multilayered films has a low sensitivity to a magnetic field component in the Y direction perpendicular to the layer, and has a high sensitivity to magnetic field components in the X and Z directions within the layer. Especially, the element shows a greatly high sensitivity to the magnetic field component in the Z direction.

As understood from FIG. 3, in the GMR element 31, each layer is parallel to the directions (X and Z directions) within a plane including a pair of current lines 11a and 11b (a planar plane of the exciting coil). Especially, in the present embodiment, the pinned layer 42 or 42' is magnetized in parallel to the direction (Z direction) along which the pair of current lines 11a and 11b is elongated, and the free layer 40 or 40' under the condition without any external magnetic field is magnetized perpendicularly to the direction along which the pair of current lines 11a and 11b is elongated and in the direction (X direction) within a plane including the lines (a planar plane of the exciting coil).

Figure 5A:
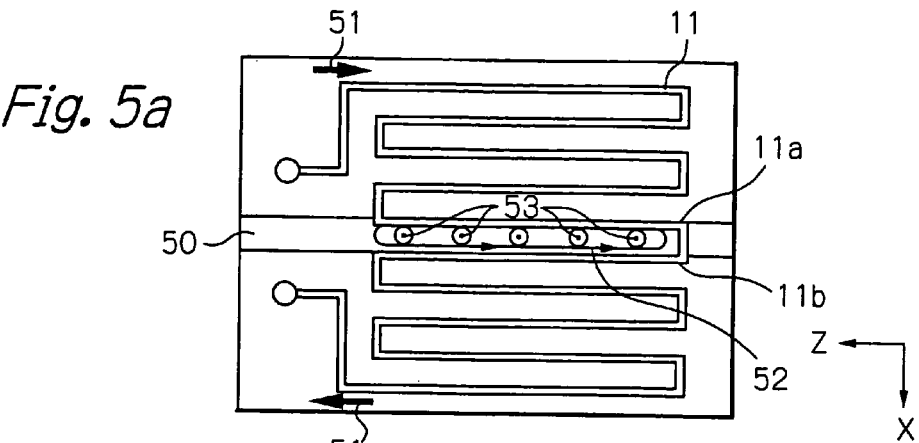
FIGS. 5a and 5b show top views for explaining the principle of checking the connection of wirings in a printed circuit board using the eddy-current sensor for nondestructive testing according to the embodiment shown in FIG. 1.
Figure 5B:
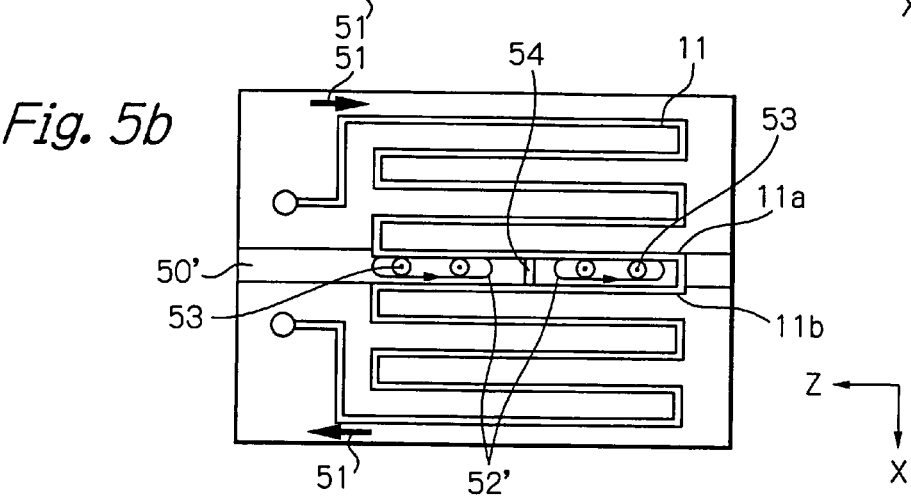
Figure 6A:
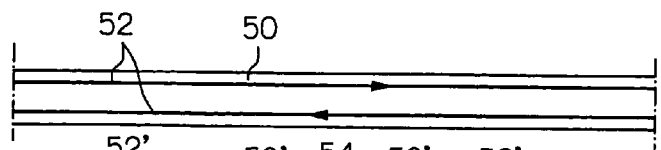
FIGS. 6a and 6b show top views indicated by magnifying only the part of the wirings in the printed circuit board shown in FIGS. 5a and 5b.
Figure 6B:
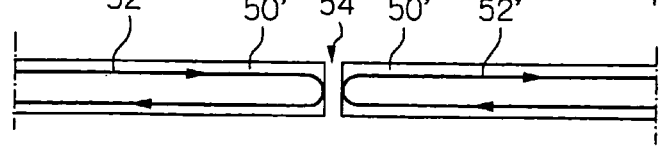

FIGS. 5a and 5b show top views for explaining the principle of checking the connection of wirings in a printed circuit board using the eddy-current sensor for nondestructive testing according to the present embodiment. FIGS. 6a and 6b show top views indicated by magnifying only the part of the wirings in the printed circuit board.

When checking the connection of wirings, the eddy-current sensor for nondestructive testing is two-dimensionally scanned in parallel with the surface of the printed circuit board as a subject under the condition where radio frequency current flows in the exciting coil 11. In this state, the output of the GMR element is detected under the condition where a sense current flows through the element.

We now consider the case, as shown in FIGS. 5a and 5b, where the wiring 50 on the printed circuit board and the current lines of the eddy-current sensor for nondestructive testing are parallel with each other, and the wiring 50 is positioned between the current lines 11a and 11b. FIGS. 5a and 6a show a case without any breaking of the wiring 50, and FIGS. 5b and 6b show a case with a breaking of the wiring 50.

As shown in FIG. 5a, a radio frequency exciting current 51 induces an eddy-current 52 in the wiring 50 along the wiring's direction. FIG. 6a also shows this state. As shown in FIG. 5a, the eddy-current 52 induces a new magnetic field (eddy-current-induced magnetic field) 53, and then the GMR element generates an output voltage according to the X component of the magnetic field 53.

When the wiring 50' has a breaking 54, the eddy-current 52' is returned just before the breaking 54, as shown in FIGS. 5b and 6b. Consequently, an incremental eddy-current flows, generated by the returned eddy-current 52', and then the eddy-current-induced magnetic field at the breaking is changed. The GMR element generates an output voltage according to the X component of the changed eddy-current-induced magnetic field.

According to the present embodiment, a plurality of thin-film chips 14 to 18 each of which includes the GMR element are used as a means of detecting the magnetic field generated by the change of the eddy current. Therefore, only a slight change of the eddy-current direction can be detected with greatly high sensitivity, even when the thin-film chips are set on the opposite side to a subject in relation to the exciting coil 11 in order to prevent a protrusion from being formed on the near side to the subject. Further, a detecting resolution can also be highly improved because of the great miniaturization of the detecting means. Furthermore, because the GMR element has a small magnetic moment and an excellent magnetic response, the exciting frequency can be set at a high value. Therefore, a high speed scanning can be performed, and a test speed under the higher resolution can be prevented from decreasing. Consequently, nondestructive testing showing high sensitivity, high testing speed, high resolution and high reliability with high signal-noise ratio can be performed.

Figure 7:
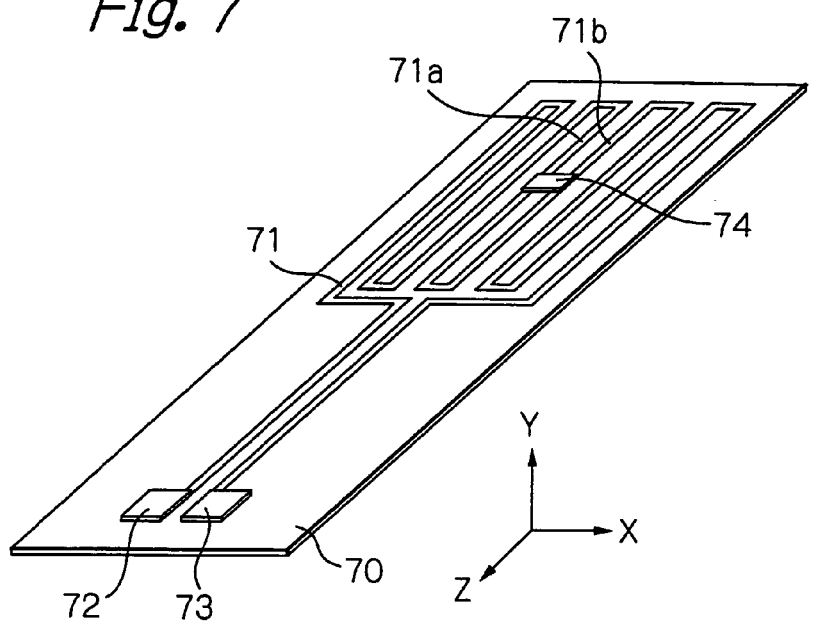
FIG. 7 shows a perspective view schematically illustrating a configuration of an eddy-current sensor for nondestructive testing according to another embodiment of the present invention.

FIG. 7 shows a perspective view schematically illustrating a configuration of an eddy-current sensor for nondestructive testing according to another embodiment of the present invention.

In this figure, reference numeral 70 indicates a substrate formed of an insulating material, 71 indicates meander-type exciting coil including coil conductors formed as the planar pattern turned back on the substrate 70, 72 and 73 indicate a pair of electrode terminals, formed on the substrate 70 and connected electrically to both ends of the exciting coil 71, 74 indicates a thin-film chip, bonded on the exciting coil 71 and mounted with a GMR element such as an SVMR element.

The exciting coil 71 includes a coil conductor layer formed on the insulative substrate 70 and an insulating layer that covers the coil conductor layer, as well as the embodiment in FIG. 1. An exciting part of the exciting coil 71 has a plurality of current lines that extend in parallel with each other to Z direction on substrate 70, and are turned back at both ends. During the testing, alternative exciting currents with opposite directions to each other flow through the current lines adjacent to each other, respectively.

The thin film chip 74 is set on a central axis of a pair of current lines 71a and 71b positioned at the center in the X direction on the exciting coil 71. The surface opposite to a visible surface of the substrate 70 in FIG. 7 faces a subject. Therefore, the thin film chip 74 is bonded on the opposite surface to the subject in relation to the exciting coil 71.

As clarified from the above descriptions, the embodiment in FIG. 7 has almost the same configuration as the embodiment in FIG. 1, except that the embodiment in FIG. 7 includes not a plurality of the thin-film chips but a single thin-film chip. Therefore, the explanation of the function and effect of the present embodiment will be omitted.

Figure 8:
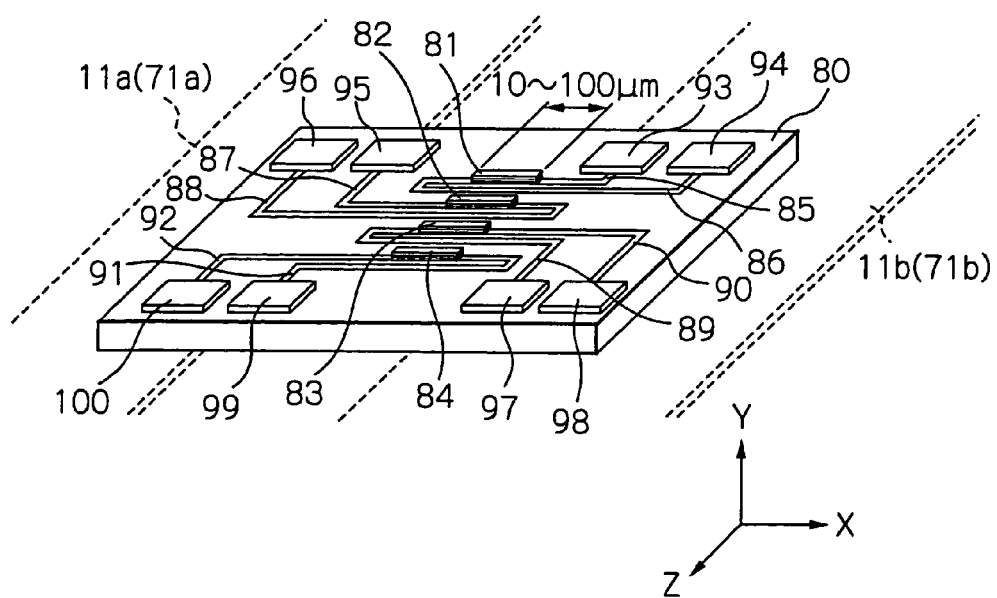
FIG. 8 shows a perspective view schematically illustrating an alternative of the thin-film chip configuration according to the embodiment shown in FIG. 1 or 7.

FIG. 8 shows a perspective view schematically illustrating an alternative of thin-film chip configuration according to the embodiment shown in FIG. 1 or 7. To be easily understood, the GMR elements are described with exaggeration in FIG. 8.

In this alternative, the thin-film chip includes, for example, four GMR elements 81 to 84 such as SVMR elements, four pairs of lead conductors 85 and 86, 87 and 88, 89 and 90, and 91 and 92 connected electrically to the GMR elements 81 to 84 respectively, and four pairs of electrode terminals 93 and 94, 95 and 96, 97 and 98, and 99 and 100 connected electrically to these lead conductors respectively, all of which are formed by thin-film technique on a chip substrate 80.

A film-structure of a main part of the SVMR element for an example of each of the GMR elements 81 to 84 is the same as shown in FIGS. 4a and 4b. That is to say, the main part of the SVMR element is formed of an SVMR multi-layered film in which a free layer 40 made of a ferromagnetic material, a spacer layer 41 made of a non-magnetic conductive material, a pinned layer 42 made of a ferromagnetic material and a pinning layer 43 made of an antiferromagnetic material are laminated in this order from the substrate side, or is formed of an SVMR multilayered film in which a pinning layer 43' made of an antiferromagnetic material, a pinned layer 42' made of a ferromagnetic material, a spacer layer 41' made of a non-magnetic conductive material and a free layer 40' made of a ferromagnetic material are laminated in this order from the substrate side. In the SVMR multilayered film, the pinned layer 42 or 42' and pinning layer 43 or 43' are magnetized to the in-plane −Z direction of the layers, and the free layer 40 or 40' under the condition without any external magnetic field is magnetized to the in-plane +X direction of the layer.

The SVMR element formed of such multilayered films has a low sensitivity to a magnetic field component in the Y direction perpendicular to the layer, and has a high sensitivity to magnetic field components in the X and Z directions within the layer. Especially, the element shows a greatly high sensitivity to the magnetic field component in the Z direction.

As understood from FIG. 8, in each of the GMR elements 81 to 84, each layer is parallel to the directions (X and Z direction) within a plane including a pair of current lines 11a and 11b (a planar plane of the exciting coil). Especially, in the present embodiment, the pinned layer 42 or 42' is magnetized in parallel to the direction (Z direction) along which the pair of current lines 11a and 11b (71a and 71b) is elongated, and the free layer 40 or 40' under the condition without any external magnetic field is magnetized perpendicularly to the direction along which the pair of current lines 11a and 11b (71a and 71b) is elongated and in the direction (X direction) within a plane including the lines (a flat plane of the exciting coil).

In the above-mentioned embodiments, the thin-film chip includes the GMR element such as the SVMR element. However, it is evident that the thin-film chip may include a TMR element instead of the GMR element, which has higher sensitivity than the GMR element.

The eddy-current sensor for nondestructive testing according to the present invention is extremely useful for a remarkably fine nondestructive testing such as an inspection of the micro-defects in an object's surface and inside and an inspection of the micropatterns on a printed circuit board, as well as nondestructive testing of important metal machine parts of a nuclear power plant, an aircraft and so on.

All the foregoing embodiments are by way of example of the present invention only and not intended to be limiting, and many widely different alternations and modifications of the present invention may be constructed. Accordingly, the present invention is limited only as defined in the following claims and equivalents thereto.

The invention claimed is:

1. An eddy-current sensor for nondestructive testing, comprising:
   a planar exciting coil of meander-type at least having a pair of current lines in parallel with each other through which exciting currents flow in opposite directions to each other during the testing, for generating an alternative magnetic field applied to a subject to be nondestructively tested by said exciting currents, and
   at least one spin-valve magnetoresistive element comprising a multilayered film laminated in parallel with a planar plane of said exciting coil, and positioned on a central axis between said pair of current lines and on the opposite side to said subject in relation to said exciting coil, for detecting a magnetic field generated from said subject by an eddy-current induced by said alternative magnetic field,
   said multilayered film including a free-magnetization-direction layer magnetized perpendicularly to said pair of current lines under a condition without any external magnetic field and a pinned-magnetization-direction layer magnetized in parallel with said pair of current lines.

2. The sensor as claimed in claim 1, wherein said at least one spin-valve magnetoresistive element is a single spin-valve magnetoresistive element positioned on a central axis between said pair of current lines.

3. The sensor as claimed in claim 1, wherein said at least one spin-valve magnetoresistive element is a plurality of spin-valve magnetoresistive elements aligned on a central axis between said pair of current lines.

4. The sensor as claimed in claim 1, wherein said at least one spin-valve magnetoresistive element is a single spin-valve magnetoresistive element, and the sensor comprises at least one thin-film chip comprising a chip substrate, said single spin-valve magnetoresistive element formed on said chip substrate, and a pair of electrode terminals connected to both ends of said single spin-valve magnetoresistive element, and said at least one thin-film chip is bonded on said exciting coil.

5. The sensor as claimed in claim 4, wherein said at least one thin-film chip is a single thin-film chip, positioned on a central axis between said pair of current lines and bonded on said exciting coil.

6. The sensor as claimed in claim 4, wherein said at least one thin film chip is a plurality of thin-film chips, aligned on a central axis between said pair of current lines and bonded on said exciting coil.

7. The sensor as claimed in claim 1, wherein said at least one spin-valve magnetoresistive element is a plurality of spin-valve magnetoresistive elements, and the sensor comprises at least one thin-film chip comprising a chip substrate, said plurality of spin-valve magnetoresistive elements formed on said chip substrate, and a plurality of pairs of electrode terminals connected respectively to both ends of said plurality of spin-valve magnetoresistive elements, and said at least one thin-film chip is bonded on said exciting coil.

8. The sensor as claimed in claim 7, wherein said exciting coil comprises a coil conductor layer formed on a substrate and an insulating layer covering said coil conductor layer.

9. The sensor as claimed in claim 7, wherein said at least one thin-film chip is a single thin-film chip, positioned on a central axis between said pair of current lines and bonded on said exciting coil.

10. The sensor as claimed in claim 7, wherein said at least one thin film chip is a plurality of thin-film chips, aligned on a central axis between said pair of current lines and bonded on said exciting coil.

* * * * *